United States Patent
Ma et al.

(10) Patent No.: US 12,073,555 B2
(45) Date of Patent: Aug. 27, 2024

(54) INSPECTION OF REFLECTIVE SURFACES BASED ON IMAGE CORRELATION

(71) Applicant: GM GLOBAL TECHNOLOGY OPERATIONS LLC, Detroit, MI (US)

(72) Inventors: Zerun Ma, Shanghai (CN); Guangze Li, Novi, MI (US); Hui-ping Wang, Troy, MI (US); Yan Cai, Shanghai (CN); Blair E. Carlson, Ann Arbor, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 299 days.

(21) Appl. No.: 17/666,939

(22) Filed: Feb. 8, 2022

(65) Prior Publication Data

US 2023/0214988 A1 Jul. 6, 2023

(30) Foreign Application Priority Data

Jan. 5, 2022 (CN) .......................... 202210004406.1

(51) Int. Cl.
| | |
|---|---|
| *G06T 7/00* | (2017.01) |
| *G01B 11/22* | (2006.01) |
| *G01N 21/95* | (2006.01) |
| *G01N 33/207* | (2019.01) |
| *G06T 7/521* | (2017.01) |
| *H04N 23/56* | (2023.01) |
| *H04N 23/90* | (2023.01) |

(52) U.S. Cl.
CPC .............. *G06T 7/001* (2013.01); *G01B 11/22* (2013.01); *G01N 21/95* (2013.01); *G01N 33/207* (2019.01); *G06T 7/521* (2017.01); *H04N 23/56* (2023.01); *H04N 23/90* (2023.01); *G06T 2207/20081* (2013.01)

(58) Field of Classification Search
CPC ........ G06T 7/001; G06T 7/521; G01N 33/207
See application file for complete search history.

(56) References Cited

U.S. PATENT DOCUMENTS

| | | | | |
|---|---|---|---|---|
| 2012/0330447 | A1* | 12/2012 | Gerlach | G01B 11/24 382/128 |
| 2015/0002704 | A1* | 1/2015 | Vidal-Naquet | G06T 7/337 348/241 |
| 2015/0348253 | A1* | 12/2015 | Bendall | H04N 7/183 348/86 |
| 2016/0349043 | A1* | 12/2016 | Lee | G01B 11/22 |
| 2017/0054966 | A1* | 2/2017 | Zhou | H04N 13/106 |
| 2018/0374186 | A1* | 12/2018 | McMurrough | G06T 7/70 |
| 2023/0281919 | A1* | 9/2023 | Jiang | G06T 7/55 382/100 |

* cited by examiner

*Primary Examiner* — Jayanti K Patel
*Assistant Examiner* — Christopher Kingsbury Glover
(74) *Attorney, Agent, or Firm* — CANTOR COLBURN LLP

(57) ABSTRACT

A system for inspecting a reflective surface includes a first imaging assembly configured to take a first image of the reflective surface. The first image includes depth information. The system also includes a second imaging assembly configured to take a second image of the reflective surface. The second image includes contrast information. The system further includes a processor configured to acquire the first image and the second image, estimate a depth profile of the surface based on the depth information, correlate the depth profile with the second image, and identify a feature of the reflective surface based on the correlation.

20 Claims, 10 Drawing Sheets

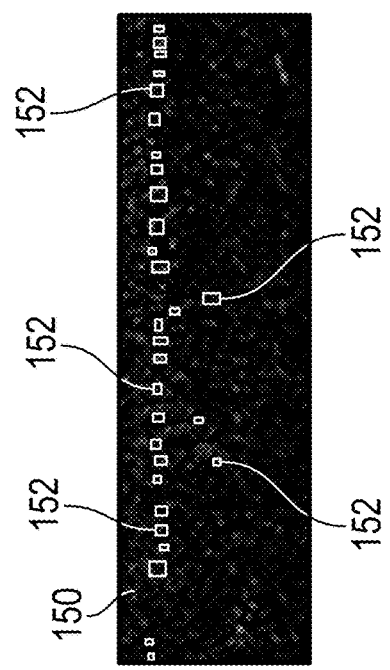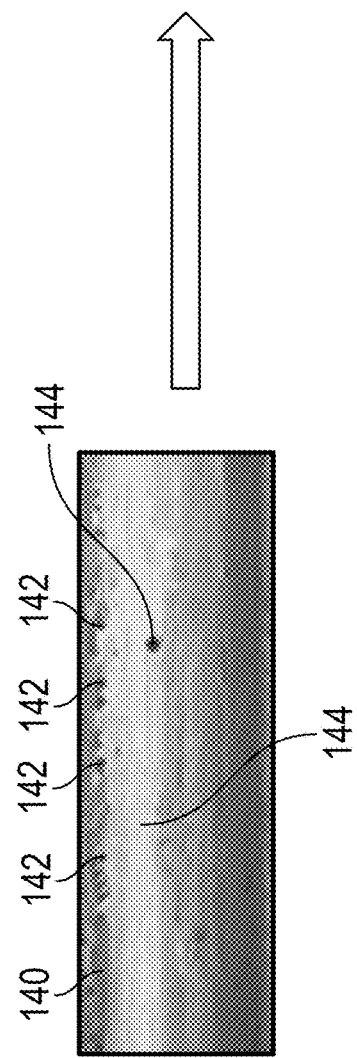
FIG. 9

INSPECTION OF REFLECTIVE SURFACES BASED ON IMAGE CORRELATION

CROSS REFERENCE TO RELATED APPLICATIONS

This application claims the benefit of Chinese Patent Application No. 202210004406.1, filed Jan. 5, 2022, the disclosure of which is incorporated herein by reference in its entirety.

INTRODUCTION

The subject disclosure relates to inspection of surfaces, and more particularly to inspection of reflective surfaces to identify defects, discontinuities and/or other features.

In automotive and other industries, various types of joining techniques are used to assemble various components. An example of such a joining technique is laser brazing. Brazed surfaces are often polished right after brazing for improved surface aesthetics and become highly reflective to optical lighting. Laser braze joints are typically inspected to ensure that the laser braze surfaces of such joints are free from defects that could reduce the effectiveness and affect the aesthetics of the surfaces. Defects can have various sizes and shapes, which in some cases can be difficult to detect. It is desirable to have a system and method for inspecting laser braze surfaces and other reflective surfaces that is able to effectively identify surface defects.

SUMMARY

In one exemplary embodiment, a system for inspecting a reflective surface includes a first imaging assembly configured to take a first image of the reflective surface, the first image including depth information, a second imaging assembly configured to take a second image of the reflective surface, the second image including contrast information, and a processor configured to acquire the first image and the second image. The processor is configured to perform: estimating a depth profile of the reflective surface based on the depth information, correlating the depth profile with the second image, and identifying a feature of the reflective surface based on the correlation.

In addition to one or more of the features described herein, the reflective surface is a braze joint surface.

In addition to one or more of the features described herein, correlating the depth profile with the second image includes constructing an image having an image attribute that is based on the depth profile.

In addition to one or more of the features described herein, the first imaging assembly includes a first camera and a laser oriented toward the reflective surface, the laser configured to project a laser line on the reflective surface, the first image including a series of images, each of the series of images depicting the laser line at a plurality of locations along the reflective surface.

In addition to one or more of the features described herein, the depth profile is estimated based on based on a laser triangulation technique.

In addition to one or more of the features described herein, the second imaging assembly includes a second camera and an illumination device configured project a diffuse light beam on the reflective surface.

In addition to one or more of the features described herein, the first imaging assembly and the second imaging assembly are in a fixed position relative to one another, and the first imaging assembly and the second imaging assembly are configured to be scanned along the reflective surface and take the first image and the second image simultaneously.

In addition to one or more of the features described herein, the illumination device is disposed at a selected distance from the reflective surface, and is oriented according to a selected angle relative to the reflective surface.

In addition to one or more of the features described herein, the selected distance and the selected angle is determined by taking a plurality of reference images of a reference surface, each of the plurality of reference images taken with a respective combination of a distance value and an angle value, calculating an intensity distribution of each reference image, estimating a homogeneity of each reference image based on the intensity distribution, determining a reference image having a highest homogeneity, selecting the distance value associated with the determined reference image as the selected distance, and selecting the angle value associated with the determined reference image as the selected angle.

In addition to one or more of the features described herein, identifying the feature includes selecting an image window corresponding to a section of the constructed image, the image window having a size selected based on an expected size of the feature.

In one exemplary embodiment, a method of inspecting a reflective surface includes taking a first image of the reflective surface by a first imaging assembly, the first image including depth information, and taking a second image of the reflective surface by a second imaging assembly, the second image including contrast information. The method also includes estimating a depth profile of the reflective surface based on the depth information, correlating the depth profile with the second image, and identifying a feature of the reflective surface based on the correlation.

In addition to one or more of the features described herein, correlating the depth profile with the second image includes constructing an image having an image attribute that is based on the depth profile.

In addition to one or more of the features described herein, the first imaging assembly includes a first camera and a laser oriented toward the reflective surface, the laser configured to project a laser line on the reflective surface, wherein taking the first image includes taking a series of images, each of the series of images depicting the laser line at a plurality of locations along the reflective surface.

In addition to one or more of the features described herein, the second imaging assembly includes a second camera and an illumination device configured project a diffuse light beam on the reflective surface, the second image taken when the illumination device is disposed at a selected distance from the reflective surface, and is oriented according to a selected angle relative to the reflective surface.

In addition to one or more of the features described herein, the selected distance and the selected angle is determined by performing: taking a plurality of reference images of a reference surface, each of the plurality of reference images taken with a respective combination of a distance value and an angle value, calculating an intensity distribution of each reference image, estimating a homogeneity of each reference image based on the intensity distribution, determining a reference image having a highest homogeneity, selecting the distance value associated with the determined reference image as the selected distance, and selecting the angle value associated with the determined reference image as the selected angle.

In addition to one or more of the features described herein, identifying the feature includes selecting an image window corresponding to a section of the constructed image, the image window having a size selected based on an expected size of the feature.

In addition to one or more of the features described herein, the size of the window is selected based on a machine learning model.

In one exemplary embodiment, a computer program product includes a computer readable storage medium, the computer readable storage medium having instructions executable by a computer processor to cause the computer processor to perform a method. The method includes taking a first image of a reflective surface by a first imaging assembly, the first image including depth information, and taking a second image of the reflective surface by a second imaging assembly, the second image including contrast information. The method also includes estimating a depth profile of the reflective surface based on the depth information, correlating the depth profile with the second image, and identifying a feature of the reflective surface based on the correlation.

In addition to one or more of the features described herein, the first imaging assembly includes a first camera and a laser oriented toward the reflective surface, the laser configured to project a laser line on the reflective surface, and taking the first image includes taking a series of images, each of the series of images depicting the laser line at a plurality of locations along the reflective surface.

In addition to one or more of the features described herein, the second imaging assembly includes a second camera and an illumination device configured project a diffuse light beam on the reflective surface, the second image taken when the illumination device is disposed at a selected distance from the reflective surface, and is oriented according to a selected angle relative to the reflective surface.

The above features and advantages, and other features and advantages of the disclosure are readily apparent from the following detailed description when taken in connection with the accompanying drawings.

BRIEF DESCRIPTION OF THE DRAWINGS

Other features, advantages and details appear, by way of example only, in the following detailed description, the detailed description referring to the drawings in which:

FIG. 9 depicts an example of a feature of interest and a window used to identify the feature of interest in an image;

DETAILED DESCRIPTION

Figure 1:
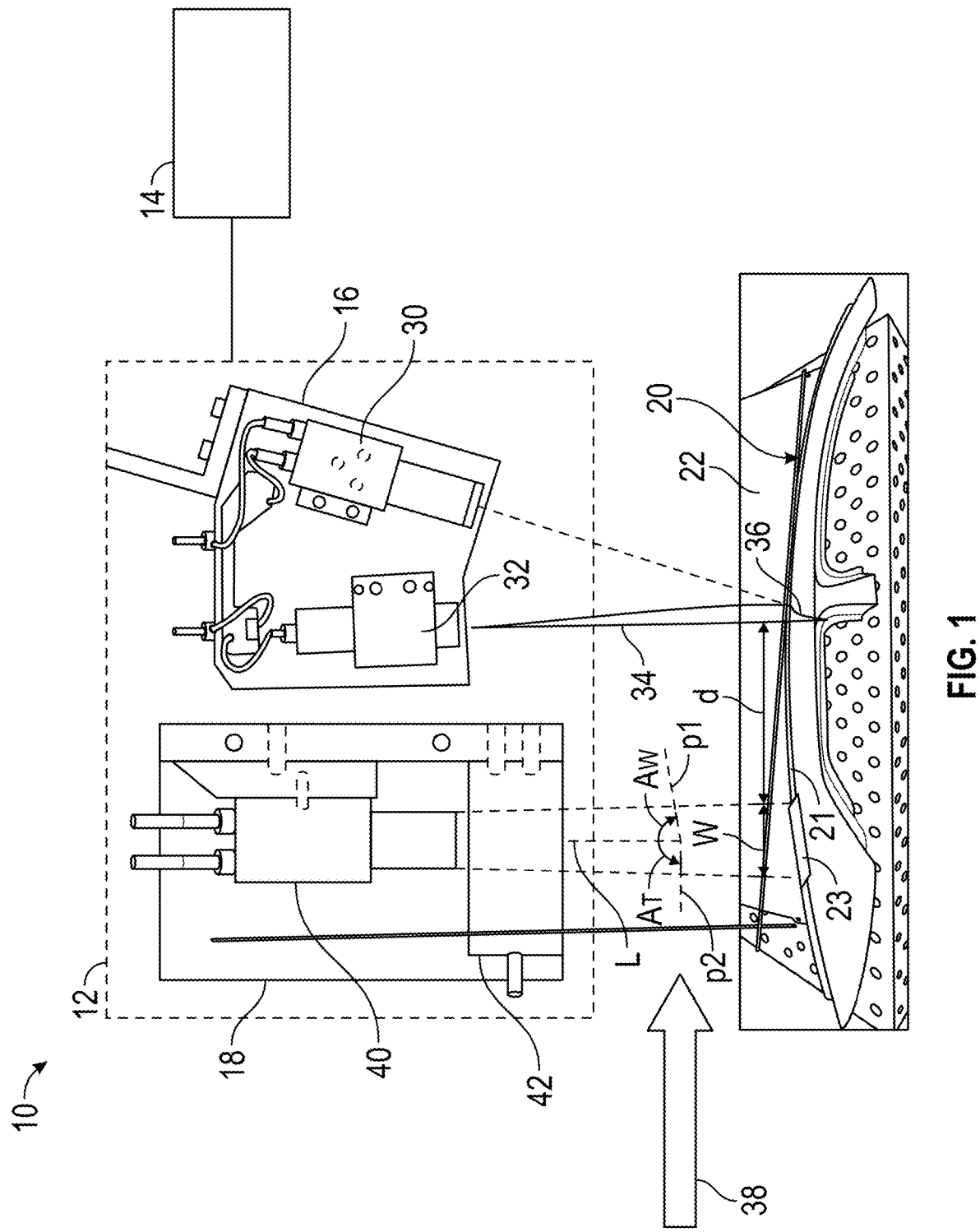
FIG. 1 depicts an embodiment of a system for inspecting a reflective surface, the system including a first imaging assembly and a second imaging assembly.

The following description is merely exemplary in nature and is not intended to limit the present disclosure, its application or uses. It should be understood that throughout the drawings, corresponding reference numerals indicate like or corresponding parts and features.

In accordance with one or more exemplary embodiments, methods, devices and systems are provided for inspecting reflective surfaces. In an embodiment, surfaces that may be inspected include highly reflective surfaces, such as surfaces of grinded and polished braze joints with low surface roughness (braze surfaces or polished braze surfaces).

An inspection system includes a first imaging assembly that is configured to take one or more first images of a reflective surface, such as one or more first images of a laser line on the reflective surface. Each of the one or more first images include depth information. "Depth" may be defined as a distance of a point on a surface from a reference plane (e.g., a plane in a direction of the surface and/or normal to an axis of the laser). In an embodiment, the first imaging assembly includes an optical camera and a laser configured to project a laser line onto a portion of the surface that is being imaged. A series of first images ("laser line images"), each displaying the laser line at a different location on the surface, may be analyzed by laser triangulation or another suitable technique to extract depth information (e.g., a surface profile or depth profile).

The inspection system also includes a second imaging assembly that is configured to take one or more second images of the surface. The second imaging assembly includes an illumination device that projects diffuse light on a portion (an "illuminated portion") of the surface. A camera takes one or more second images ("contrast images") of the illuminated portion that include contrast information (e.g., color and/or brightness contrast). The illuminated portion has an illumination area based on a width of the illuminated portion.

A processing device or system is configured to analyze the images by reconstructing or calculating a three-dimensional or two-dimensional depth profile based on the first images, and correlating the depth profile with a second image. For example, an image of a portion of the surface (a "constructed image") is constructed based on the depth profile, and the constructed image is then correlated with a second image of the portion of the surface. The constructed image and/or the second image are analyzed to identify features of interest, such as defects or discontinuities of the surface.

Embodiments may include methods for selecting operational parameters of the first imaging device. An embodiment of a method includes selecting operational parameters (e.g., illumination area size, work angle and/or travel angle)

of the first imaging device that provides homogenous illumination. Embodiments also include a method of selecting window configurations used in analyzing images for feature detection.

Embodiments described herein present numerous advantages and technical effects. The embodiments provide for an improved inspection method, which is able to detect defects that are otherwise difficult to detect via other techniques.

FIG. 1 depicts an embodiment of an inspection system 10. The inspection system 10 includes an imaging system 12 and an analysis unit 14 configured to receive images of a reflective surface, such as a surface of a laser braze joint or other joint. The imaging system 12 includes a first imaging assembly 16 that is configured to take images of the reflective surface that include depth information. The imaging system 12 also includes a second imaging assembly 18 configured to illuminate the surface and take images of the surface that include brightness and/or contrast information.

The embodiment of FIG. 1 is discussed in conjunction with an example of a reflective surface 20. In this example, the reflective surface 20 is a surface of a braze joint 21 used to attach components of a vehicle roof 22. Embodiments are not so limited, as the embodiments can be used to inspect any suitable reflective surface such as a polished laser weld joint surface, a decklid braze surface and a liftgate braze surface.

In an embodiment, the first imaging assembly 16 includes an optical camera 30 and a laser 32, which are oriented so that they both are directed at a selected region of the surface 20. For example, the laser 32 is a line laser configured to emit a laser beam 34 that projects a laser line 36 onto the surface 20. In use, the camera 30 takes an image of the surface and the laser line 36 at a plurality of locations on the surface 20 to generate a series of first images or laser line images. For example, the laser 32 emits the laser beam 34 and scans the laser line 36 across the surface 20. The laser line 36 is scanned along a scan direction represented by arrow 38, and the camera 30 takes a series of first images of the surface 20 and the laser line 36 at a plurality of locations along the scan direction.

In an embodiment, the second imaging assembly 18 includes an optical camera 40 and an illumination device 42. The illumination device 42 is oriented towards the surface 20 and is aligned with the camera 40 such that a portion 23 of the surface (an illuminated portion having an illumination area) is illuminated when the camera 40 takes an image. An example of the illumination device 42 is a diffuse on-axis light (DOAL) device, although any light source suitable for providing desired homogeneous lighting may be used. The second imaging assembly 18 is operated according to one or more operational parameters selected to increase or optimize the homogeneity of illumination. Examples of the operational parameters include illumination area size, distance between the illumination device 42 and the surface 20, and angle parameters such as work angle and/or travel angle.

The cameras may be configured to take gray scale and/or color images. For example, the camera 30 may take color images so that the laser line 36 is visible in the laser line images, and the camera 40 may take color or gray scale images. It is noted that the cameras are not limited to optical cameras and may be configured to take any suitable type of image. Examples of other types of images include infrared images.

Figure 2:
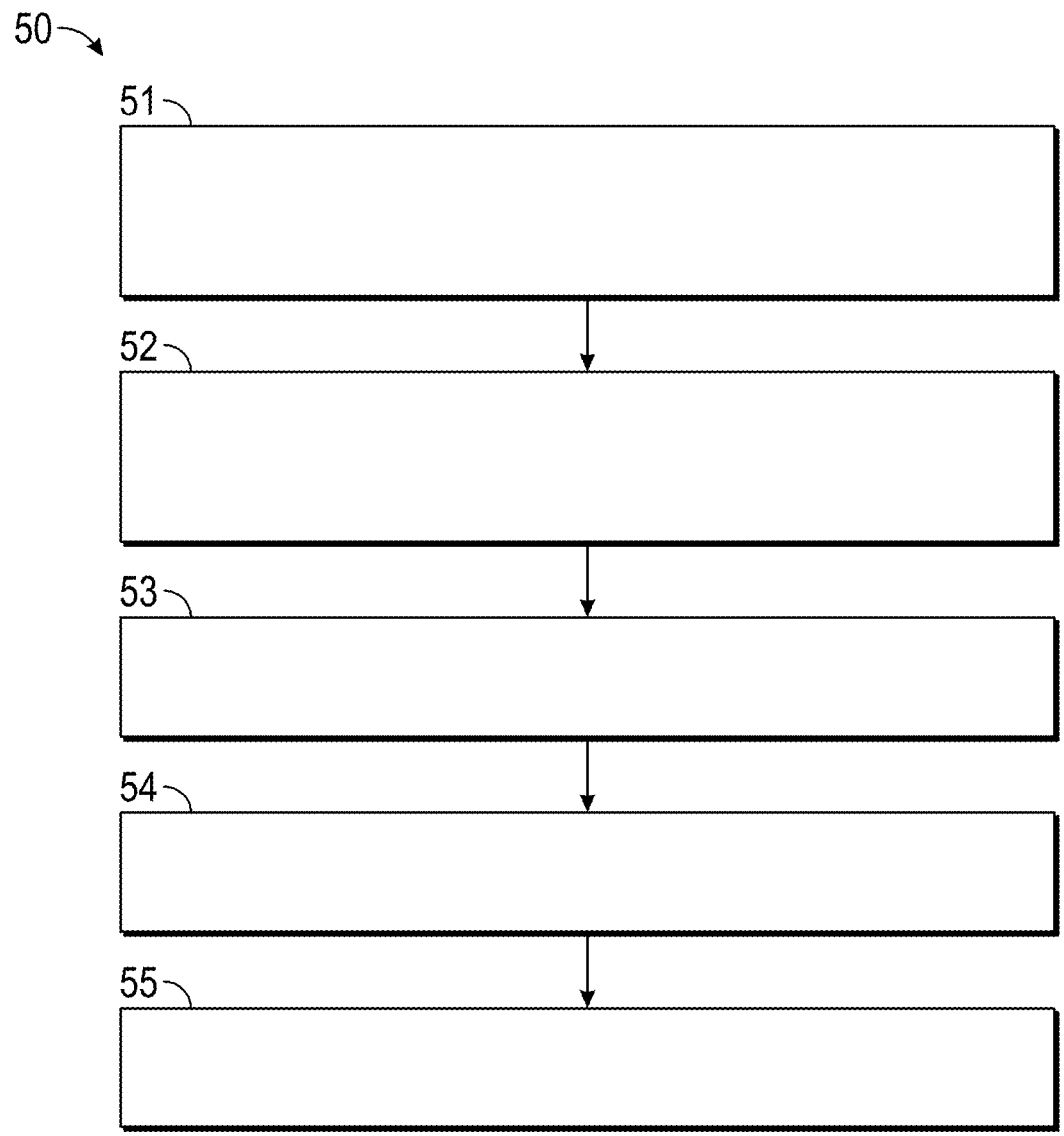
FIG. 2 is a flow diagram depicting aspects of a method of inspecting a reflective surface, according to an embodiment.

FIG. 2 illustrates an embodiment of a method 50 of inspecting a reflective surface. Aspects of the method 50 may be performed by a processor or processors, such as the analysis unit 14 and/or processing device(s) incorporated in one or more of the imaging assemblies 16 and 18. It is noted the method 50 may be performed by any suitable processing device or system, or combination of processing devices.

The method 50 includes a number of steps or stages represented by blocks 51-55. The method 50 is not limited to the number or order of steps therein, as some steps represented by blocks 51-55 may be performed in a different order than that described below, or fewer than all of the steps may be performed.

At block 51, a series of first images or laser line images of a reflective surface are taken by the first imaging assembly 16 as the imaging assembly 16 is scanned along the surface. Each of the laser line images includes an image of a laser line at various locations. The camera 30 may take images at a high frame rate (e.g., about 70 frames per second or more).

At block 52, the surface is illuminated by the illumination device 42 and at least one second image or contrast image is taken by the camera 40. Each contrast image includes contrast information, such as brightness and contrast information. For example, contrast images are taken with a low frame rate (e.g., about 5 fps) and high resolution (e.g., about 0.025 mm/pixel). The surface is illuminated using DOAL lighting, for example, which may have a color (e.g., red, green, blue) that is different than the laser color.

Contrast images are taken by the camera 40 using selected values of operational parameters, which are selected to achieve uniform lighting over illuminated portions of the surface that are being imaged. As shown in FIG. 1, such parameters include a distance between the illumination device 42 and the surface, a width (W) and/or area size of an illuminated portion, and angle of the illumination device 42 and the camera 40. In an embodiment, the selected angle includes a work angle $A_W$ and a travel angle $A_T$. The work angle $A_W$ is defined as an angle between an axis L of the light emitted by the illumination device 42 and a plane p1 tangent to the surface, and the travel angle $A_T$ is defined as an angle between the axis L and a plane p2 parallel to the scan direction.

In an embodiment, the imaging assemblies 16 and 18 are at fixed positions relative to one another, such that the imaging assemblies move together as they are scanned along the surface.

At block 53, the analysis unit 14 or other processing device estimates surface depth information based on the laser line images. In an embodiment, each of the series of laser line images is analyzed using, for example, laser line triangulation. The depth information from each laser line is assembled to generate a depth profile and/or any other data structure indicative of surface depth.

At block 54, the depth profile of the surface is correlated with contrast images taken by the camera 40. In an embodiment, a constructed image of the surface is generated using the depth profile. For example, an image is constructed having an image attribute (e.g., pixel color, shade or gray scale) that is a function of the depth. The constructed image is then correlated with a contrast image of the surface (or portion thereof). For example, one or more features of the contrast image can be initially identified (e.g., based on manual labeling or image analysis), and a corresponding feature or features can be identified in the constructed image. The constructed image and the contrast image can then be correlated by aligning corresponding features.

For feature detection (which is discussed further herein), the constructed image and/or the contrast image may be analyzed to detect features of interest. In addition, or alternatively, a composite image may be generated by combining the contrast image and the constructed image. The contrast image enhances feature detection by providing contrast information regarding potential features of interest in addition to profile information. A combination of the contrast information and the profile information provides for sharper and more detailed representations of a surface than representations acquired using only profile information or only contrast information. For example, the combined contrast information and profile information can be used to more accurately detect the size and extent of a relatively large feature, such as a pore, as compared to conventional methods, and can be used to detect smaller features that may be not be detectable by conventional methods.

Figure 3:
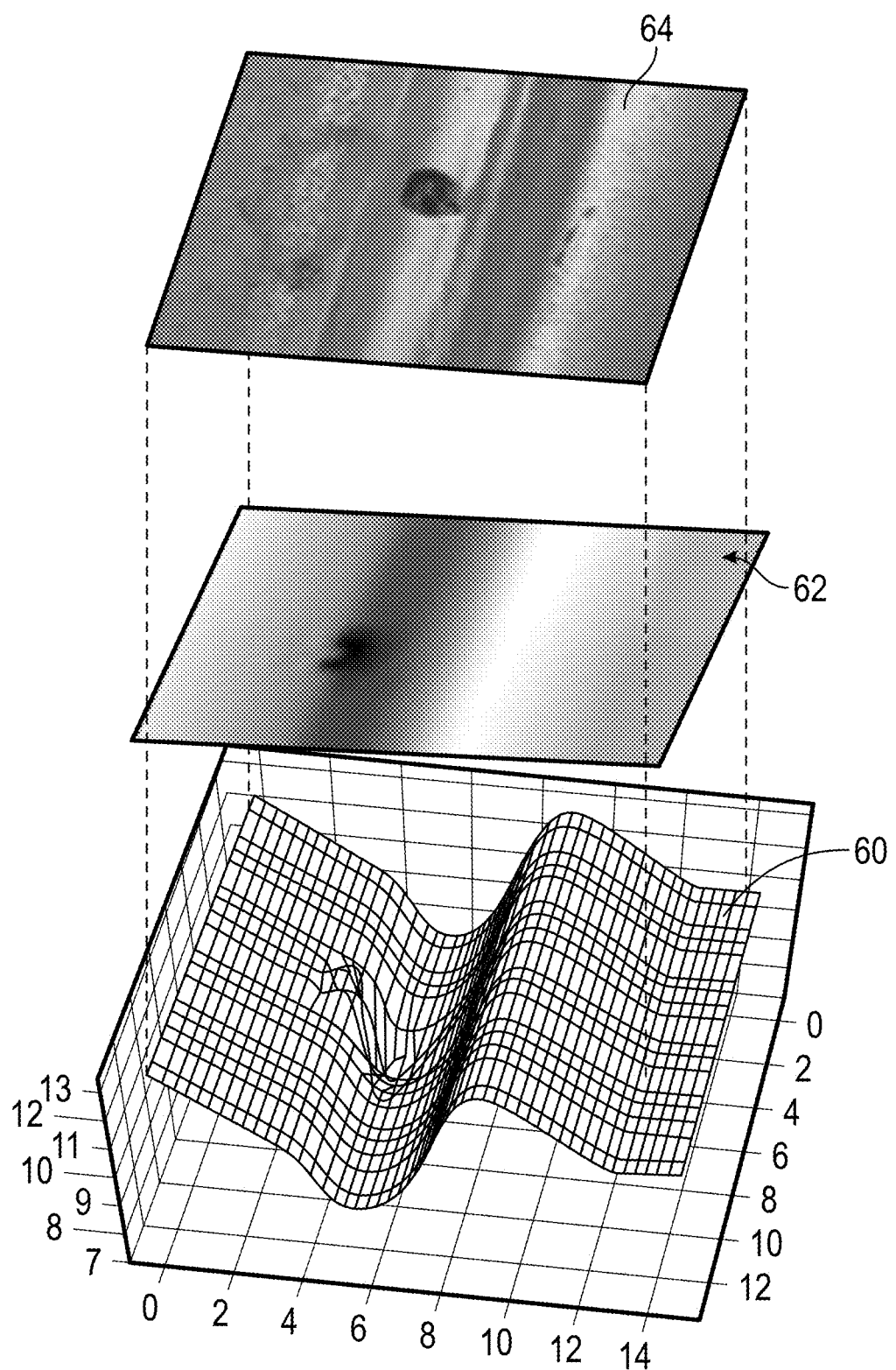
FIG. 3 depicts an example of a depth profile estimated based on images taken by the first imaging assembly, an image taken by the second imaging assembly, and an image constructed based on the depth profile.

FIG. 3 illustrates an example of image construction and correlation. In this example, the imaging assemblies 16 and 18 are scanned over a braze joint surface or other reflective surface. Laser line images are analyzed to generate a surface profile, represented by a three-dimensional graph 60. A gray scale image 62 is constructed in which shading (gray scale) is a function of profile depth. In this example, each pixel in the constructed image 62 has a shade that is a function of depth, where lower depths correspond to darker shades and higher depths correspond to lighter shades. The constructed image 62 is then correlated with a contrast image 64. The correlation may generate a composite image having one or more image attributes (e.g., color, shading) that are indicative of depth and contrast.

At block 55, images generated at blocks 51-54 (e.g., constructed images or composite images) are analyzed to detect surface features, such as defects, discontinuities and/or other features of interest. For example, a region of interest in an image (e.g., a constructed image, a contrast image and/or a composite image) is selected, and defects or other features are identified via a suitable image analysis technique, such as statistical analysis (e.g., regression) and/or machine learning (e.g., classifiers, neural networks, etc.). As discussed further herein, a windowing technique may be used in which one or more windows of selected configurations (e.g., shape and size) are determined to optimize feature detection.

Figure 4:
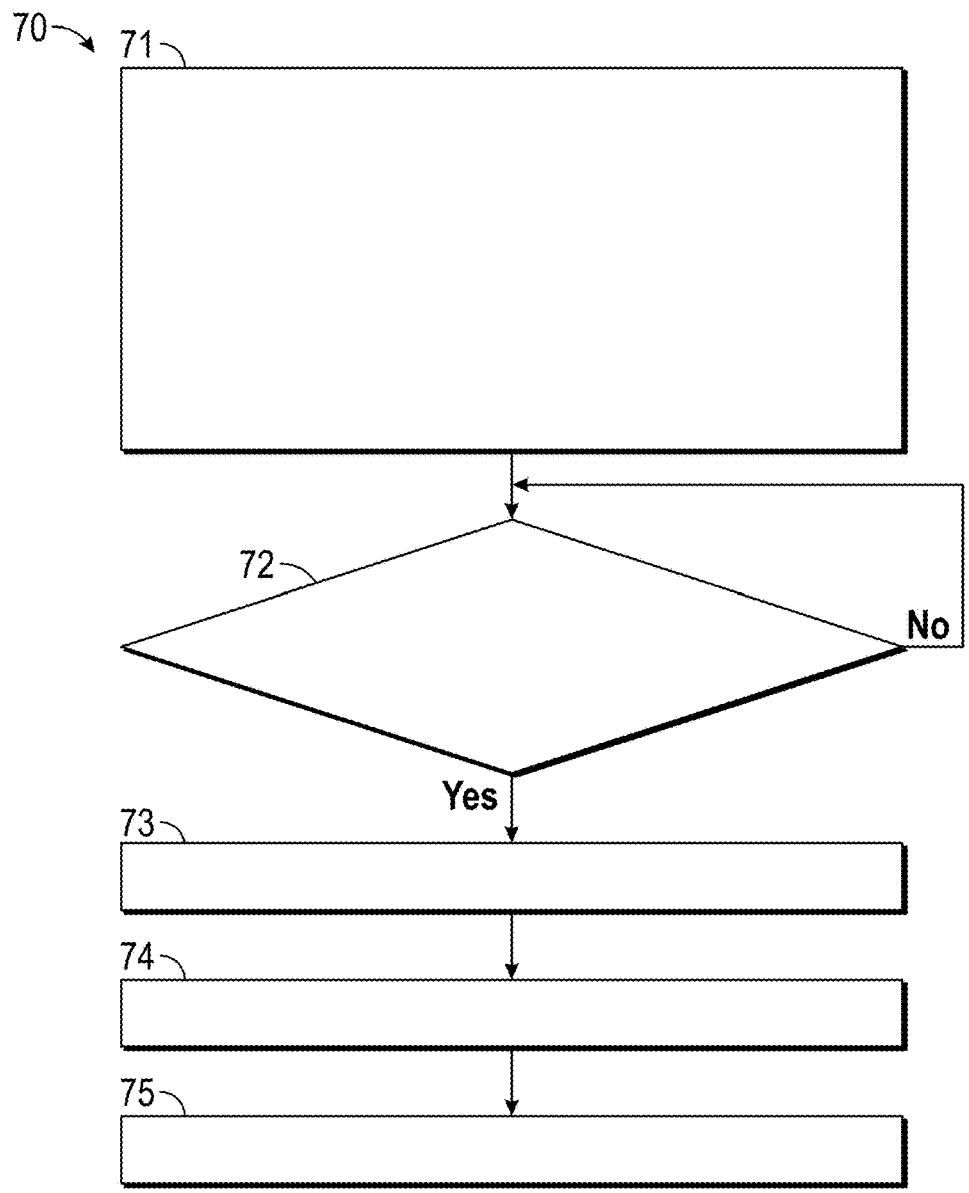
FIG. 4 is a flow diagram depicting aspects of a method of determining a depth profile based on images taken by the first imaging assembly, according to an embodiment.

FIG. 4 illustrates an embodiment of a method 70 of surface reconstruction to determine a depth profile. Aspects of the method 70 may be performed by a processor or processors, such as the analysis unit 14 and/or processing device(s) incorporated in the imaging devices. It is noted the method 70 may be performed by any suitable processing device or system, or combination of processing devices.

The method 70 includes a number of steps or stages represented by blocks 71-75. The method 70 is not limited to the number or order of steps therein, as some steps represented by blocks 71-75 may be performed in a different order than that described below, or fewer than all of the steps may be performed.

At block 71, for a given surface, contrast images of the surface taken by the second imaging assembly 18 are correlated with laser line images taken by the first imaging assembly 16. A series of gray scale contrast images and a series of laser line images are taken simultaneously as the imaging assemblies are scanned along the surface with a scan velocity v.

A contrast image of a portion of the surface, which was taken at a time $t_1$, is selected. Laser line images taken between times $t_2$ and $t_3$ are selected, so that the laser line images represent the same portion of the surface in the selected contrast image. Times $t_2$ and $t_3$ may be determined based on the following equations:

$$t_2 = t_1 - d/v, \text{ and}$$

$$t_3 = t_1 - (d+W)/v.$$

As shown graphically in FIG. 1, d is a distance between a leading end of an illuminated portion (e.g., the illuminated portion 23) and the laser beam 34. W is a width of the illuminated portion.

At block 72, the laser line images are checked to determine whether the line images were taken between times $t_2$ and $t_3$.

If so, the laser line images are selected that correspond to the contrast image of the illuminated portion of the surface.

At block 73, for each selected laser line image, a corresponding laser line is extracted. Laser line extraction may be performed using various algorithms and techniques. In an embodiment, extraction of a laser line from an image is performed using an edge detection algorithm, such as a Canny edge detection method.

An example of an edge detection method for a vertically oriented (e.g., perpendicular to a surface of interest and/or reference plane) laser line includes locating left and right edge points along the laser line in an image using a row-by-row calculation. In each row, a center point Xc of the laser line is calculated from initially estimated locations of the left and right edges of the laser line. The method then includes searching neighboring pixels of the center point Xc, where the number of neighboring pixels includes pixels covered by half of the width of the laser line in the image. A laser line edge point in a row may be defined as the position of the brightest pixel among the neighboring pixels or the average position of a selected number of the brightest pixels. Extrapolation may be used in rows with missing laser line edge points. For example, if only one edge point in a given row is detected, the center point may be defined at the position of the detected edge point, then neighboring pixels are searched to calculate the missing edge point. If both edge points are missing in a given row, the edge points may be directly extrapolated from adjacent rows above and below the given row.

At block 74, a laser line triangulation calculation is performed on the extracted laser lines to extract depth information. Laser line triangulation includes calculating a distance from various points on a laser line to the imaging assembly 16. The position of each point on the laser line and the distance is determined relative to a 2D coordinate system that is fixed relative to the imaging assembly 16.

At block 75, a surface profile of the surface portion corresponding to the contrast image is constructed. The surface profile may be a three-dimensional graph, table or other data structure indicative of profile information.

In order to achieve uniform lighting of a surface by the illumination device 18, diffuse lighting may be used. In an embodiment, the illumination area of an illuminated surface and imaging angles are selected to further enhance the uniformity of illumination.

Figure 5:
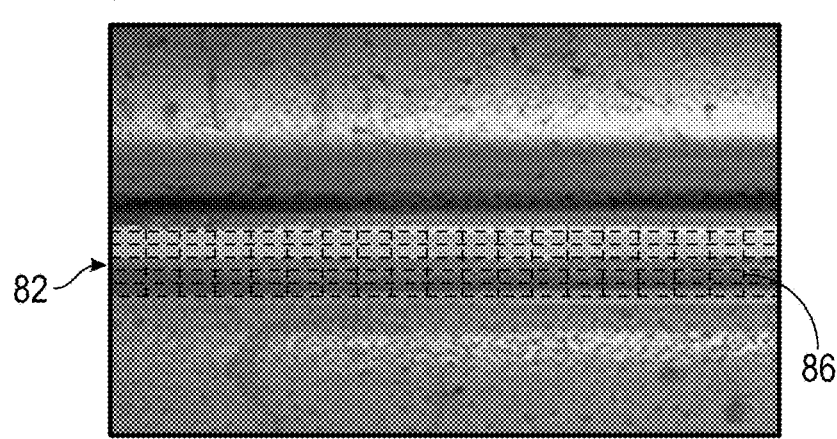
FIG. 5 depicts an example of a reference image used in an embodiment of a method of selecting operating parameters of the second imaging assembly, the operating parameters including an illumination area size and one or more angles.
Figure 6:
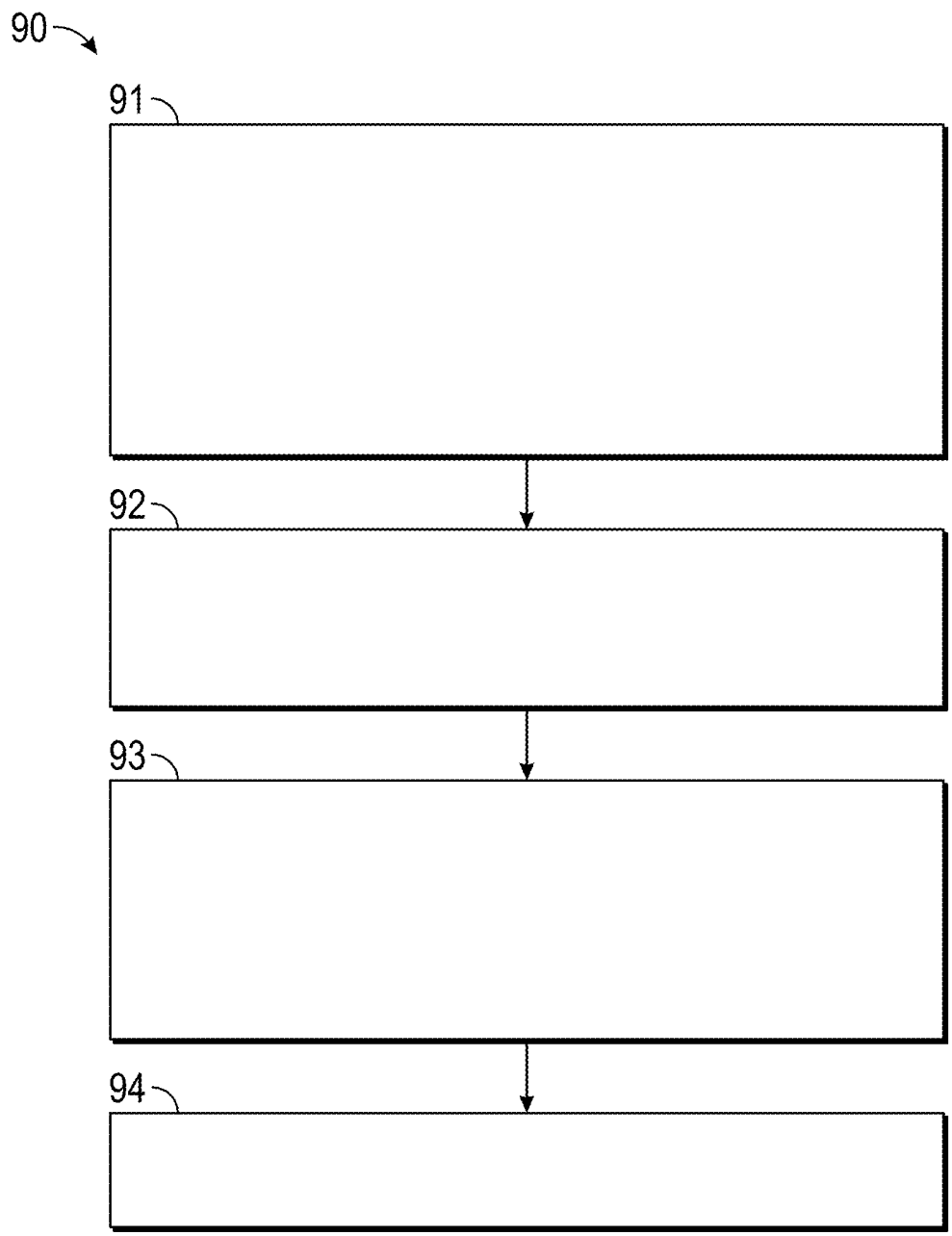
FIG. 6 is a flow diagram depicting aspects of a method of selecting operating parameters of the second imaging assembly, according to an embodiment.

FIGS. 5 and 6 depict aspects of operational parameter (e.g., area and angle) calculations. FIG. 5 depicts an example of an image of a reference surface 80. The reference surface 80 is a surface similar to the surface that is to be inspected, which is defect free or otherwise free of discontinuities or features of interest (e.g., a defect-free braze joint surface).

FIG. 6 illustrates an embodiment of a method 90 used to calculate operational parameters of the imaging device 18. Aspects of the method 90 may be performed by a processor or processors, such as the analysis unit 14 and/or processing device(s) incorporated in the imaging assemblies. It is noted the method 90 may be performed by any suitable processing device or system, or combination of processing devices.

The method 90 includes a number of steps or stages represented by blocks 91-94. The method 90 is not limited to the number or order of steps therein, as some steps represented by blocks 91-94 may be performed in a different order than that described below, or fewer than all of the steps may be performed.

At block 91, a plurality of reference images are taken by the imaging device 18. An image (or set of images) is taken for each of a plurality of combinations of illumination area size and angle parameters. In an embodiment, the combination of parameters includes work angle $A_W$ parameter values, travel angle $A_T$ parameter values and illumination area size or width. Examples of parameter values for $A_W$ and $A_T$ include zero degrees, 3 degrees, 6 degrees and others. Examples of illumination area width include widths of 50 mm and 75 mm. It is noted that these examples are provided for illustration purposes and are not intended to be limiting.

At block 92, a region of interest in each reference image is partitioned into a grid having a plurality of grid cells. For example, the reference image 80 includes a region of interest 82 in the form of a braze surface. The region of interest is partitioned into a 5×20 (5 rows, 20 columns) grid including grid cells 86.

An average pixel intensity S is estimated for each grid cell 86. The cell 86 having the highest average pixel intensity $S_{max}$ and the cell 86 having the lowest average pixel intensity $S_{min}$ are identified.

At block 93, a homogeneity of the lighting of each reference image (e.g., the reference image 80) is estimated based on the pixel intensity calculations. In an embodiment, a homogeneity value U is estimated based on the following equation:

$$U = \left(1 - \frac{S_{max} - S_{min}}{S_{max} + S_{min}}\right) \times 100\%.$$

At block 94, the image or set of images having the highest homogeneity U is identified, and the parameters associated with the identified image or set of images are selected. Inspection of other surfaces similar to the reference surface may then be performed, which includes imaging the surfaces by the imaging device 18 with the work angle, travel angle and illumination size selected at block 94.

Defects and discontinuities can vary widely in terms of size, shape and location. For example, defects typically occurring in laser braze surfaces range in size from 0.1-2 mm.

Embodiments of the inspection methods described herein may include a windowing technique, in which one or more sub-regions of a reconstructed image are selected for feature extraction. The sub-regions are also referred to as "windows," the size and shape of which may be customized for extraction of features having different sizes.

The windows are selected to facilitate accurate feature extraction. For example, selection of a window that is too large relative to surface features could result in inaccuracies due to pollution by background noise, and a window that is too small could result in missing important feature information.

Figure 7:
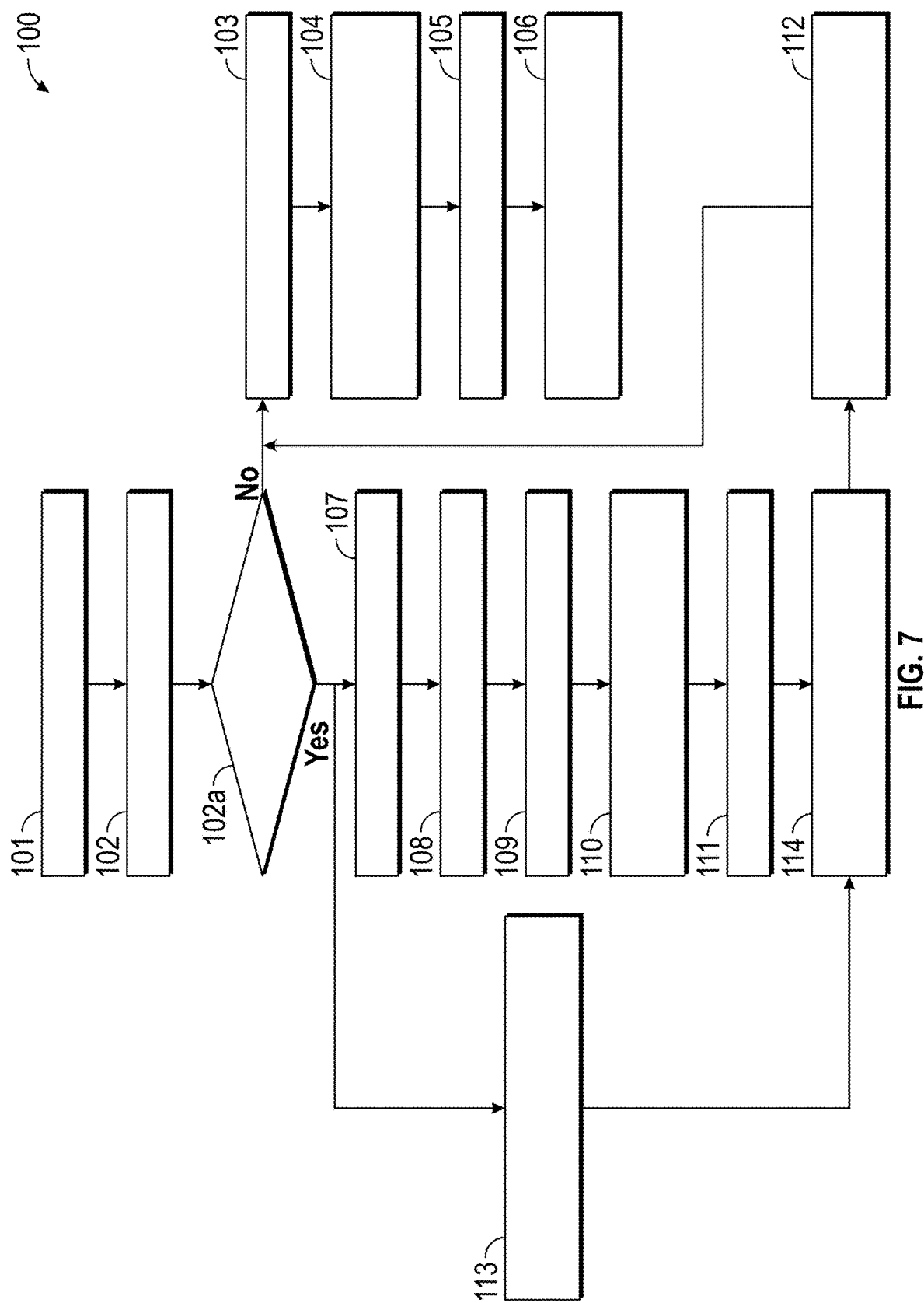
FIG. 7 is a flow diagram depicting aspects of a method of inspecting a reflective surface to identify features of interest based on images of the reflective surface, and/or selecting one or more windows used to identify features of interest in the images.

FIG. 7 is a flow diagram depicting aspects of a method 100 of window configuration selection and/or feature extraction from images (e.g., constructed images, contrast images and/or composite images). Aspects of the method 100 may be performed by a processor or processors, such as the analysis unit 14 and/or processing device(s) incorporated in the imaging assemblies. It is noted the method 100 may be performed by any suitable processing device or system, or combination of processing devices.

The method 100 includes a number of steps or stages represented by blocks 101-114. The method 100 is not limited to the number or order of steps therein, as some steps represented by blocks 101-114 may be performed in a different order than that described below, or fewer than all of the steps may be performed.

In the following, the method 100 is described in conjunction with analyzing a constructed image that includes a region of interest. The method is not so limited, as aspects of the method may be repeated for multiple images if multiple images are constructed to cover a surface that extends beyond the dimensions of a single constructed image. In addition, although the method 100 is described in conjunction with images constructed from profile information, the method can be applied to contrast images, composite images and any other images.

At block 101, imaging is performed by scanning the imaging assemblies as described herein. At block 102, profile information from laser line images and contrast information from contrast images is correlated as discussed herein to generate constructed images of a surface.

At block 102a, a decision is made as to whether to select a window configuration using a window optimization technique. If the decision is no (i.e., the optimization technique is not used), the window configuration is selected from one or more stored window configurations. If the decision is yes, the window configuration is selected based on the optimization technique described in conjunction with blocks 107-112.

At block 103, the window configuration is selected, for example, by acquiring a stored window configuration, or by selecting parameters based on the window optimization technique. In an embodiment, the window configuration includes one or more windows selected for optimized detection of defects. For example, the window configuration includes a large window having a size and shape selected to detect relatively large features. The large window may have an area that corresponds to an entirety of a region of interest (e.g., braze surface) within a constructed image. The window configuration also includes, for example, a small window having a size and shape selected to detect smaller features.

At block 104, a section of the constructed image corresponding to the window size is selected for feature extraction. If the window is smaller than the region of interest, individual sections corresponding to the window are selected so that the entire region of interest is covered. The sections may overlap based on the window configuration.

At block 105, for each window, defects or other features are extracted using any suitable technique. In an embodiment, a machine learning model is utilized, such as a support vector regression model or support vector machines (SVMs). Other types of machine learning or artificial intelligence models, or other types of classifiers, may be used.

At block 106, based on the results of feature extraction, feature information (e.g., defect identification information) is provided to a user, stored in memory or otherwise provided. It is noted that the feature or defect identification results may be used as training data to further train the machine learning model.

The method 100 may include a window optimization method represented by blocks 107-112. At blocks 107-110, window configuration parameters that can be selected for an optimized configuration are initially provided. The parameters include a number of windows at block 107 (e.g., two windows, one for larger defects and one for smaller defects), and window types (e.g., window shapes such as square, rectangular, circular) at block 108. Other window configuration parameters include window size (e.g., large and small) at block 109, and window overlap (amount of overlap between adjacent windows) at block 110.

At block 111, values for each window configuration parameter are determined, for example, by a machine learning model such as a SVM. The model may be trained using training data in the form of other images of known defects similar to those expected. The model is used to output optimal window configuration parameters based on defect or feature type and size. At block 112, the optimized configuration parameters are used as the window configuration discussed at block 103. The machine learning model may be further trained by manually labeling features of interest in the constructed image (block 113), and using the labels to further train the machine learning model (block 114).

Figure 8:
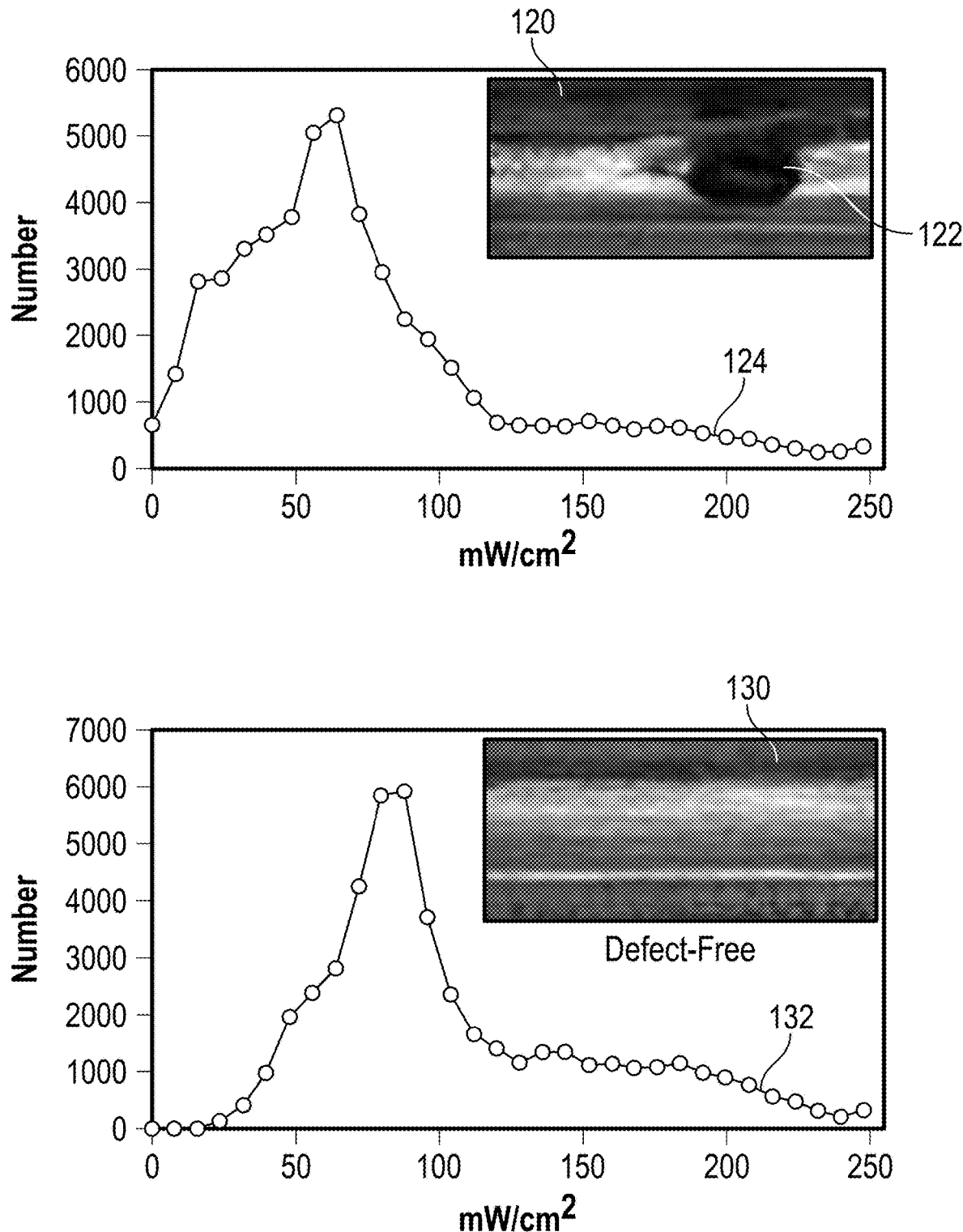
FIG. 8 depicts an example of a feature of interest and a window used to identify the feature of interest in an image.

FIGS. 8 and 9 show an example of window sizes that can be selected based on expected features or types of features. The window sizes in this example include a large window size and a small window size. Large windows are selected to facilitate detection of large features, such as large pores. Small windows are selected to facilitate detection of smaller defects, such as small pores and discontinuous edges.

FIG. 8 depicts an example of an image 120 of a large feature in the form of a pore 122, along with a histogram 124 that shows the number of pixels of various intensities measured in mW/cm$^2$. The image 120 corresponds to a large window, which encompasses the entire region of interest. For comparison, a reference image 130 of a defect free region of interest is also shown along with a corresponding histogram 132

FIG. 9 depicts an example of an image 140 of a braze surface that includes small defects. In this example, small defects in the form of sawtooth edges 142 and small pores 144 can be seen. To extract the defects, a small window is used to successively analyze sections of the image 140. In an example, a 5×5 pixel square bounding box is used. A defect identification image 150 is also shown, which shows the results of defect detection, in which individual defects are annotated with annotations 152.

Large and small are used as relative terms and are not intended to limit the windows and defects to any particular shape or size.

Figure 10:
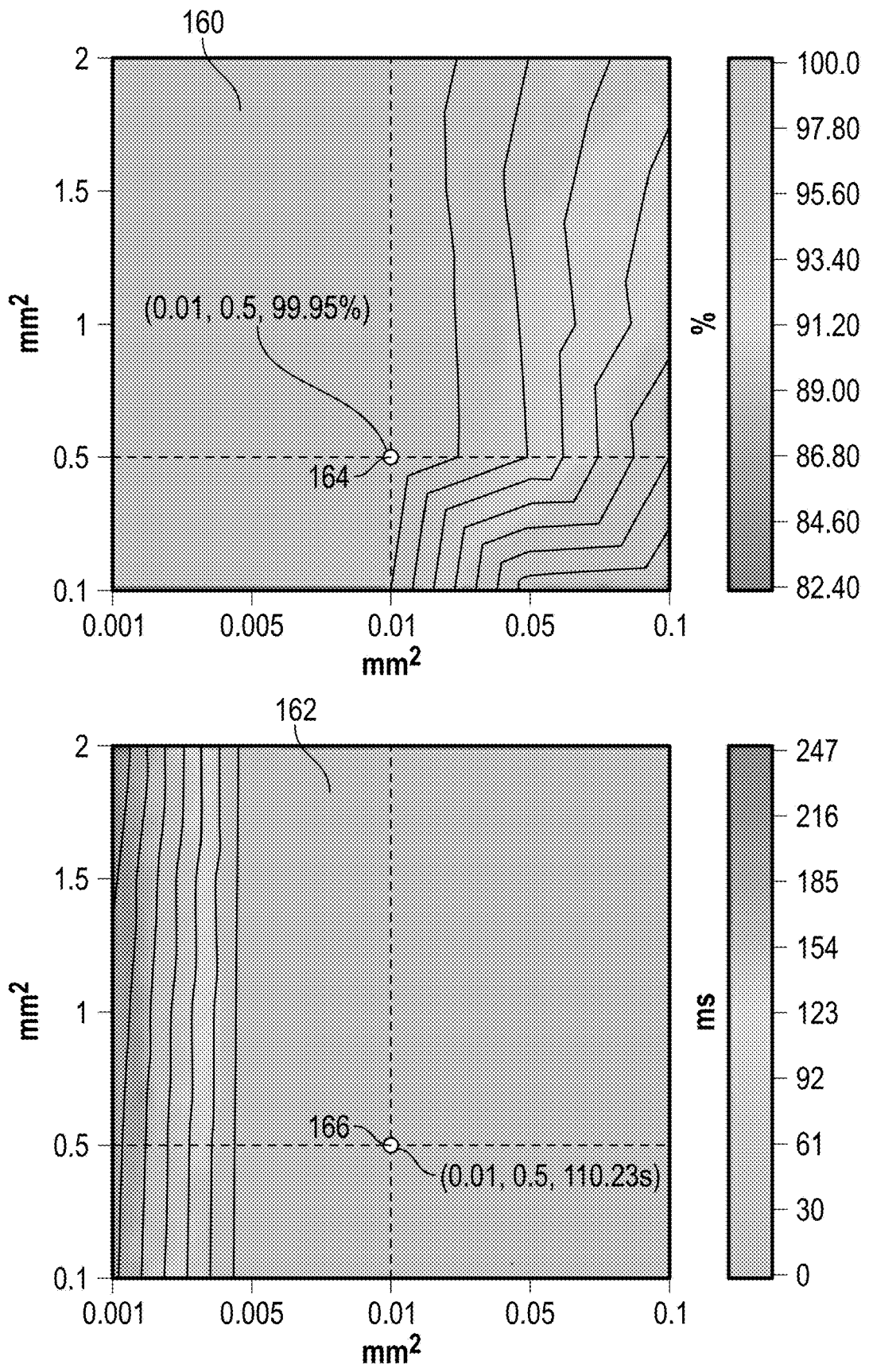
FIG. 10 depicts an example of a computation time map and an accuracy map used to select windows used to identify features of interest in an image.

Referring to FIG. 10, in an embodiment, the window optimization method includes selecting window sizes in order to optimize feature detection. The window sizes are selected to maximize accuracy while also minimizing computation time. For example, two window sizes are provided (i.e., a large window and a small window). The large window is rectangular and has an aspect ratio of 2:1, and the small window is square. For example, the large window has a selected size range of 0.1-2 mm$^2$ area, and the small window has a size range of 0.001-0.1 mm$^2$ area.

Accuracy values for different combinations of small and large window sizes are calculated, as shown by an accuracy map 160. Computation times in milliseconds (ms) for different combinations of small and large window sizes are calculated, as shown by a computation time map 162. The maps 160 and 162 are color coded. Optimized window sizes are selected that have a sufficiently low computation time while maintaining an acceptable accuracy. An example of optimized window sizes is a 0.5 mm$^2$ large window area and a 0.01 mm$^2$ small window area, which are represented as points 164 and 166. The accuracy for these sizes is 99.95%, and the computation time is 110.23 seconds.

Figure 11:
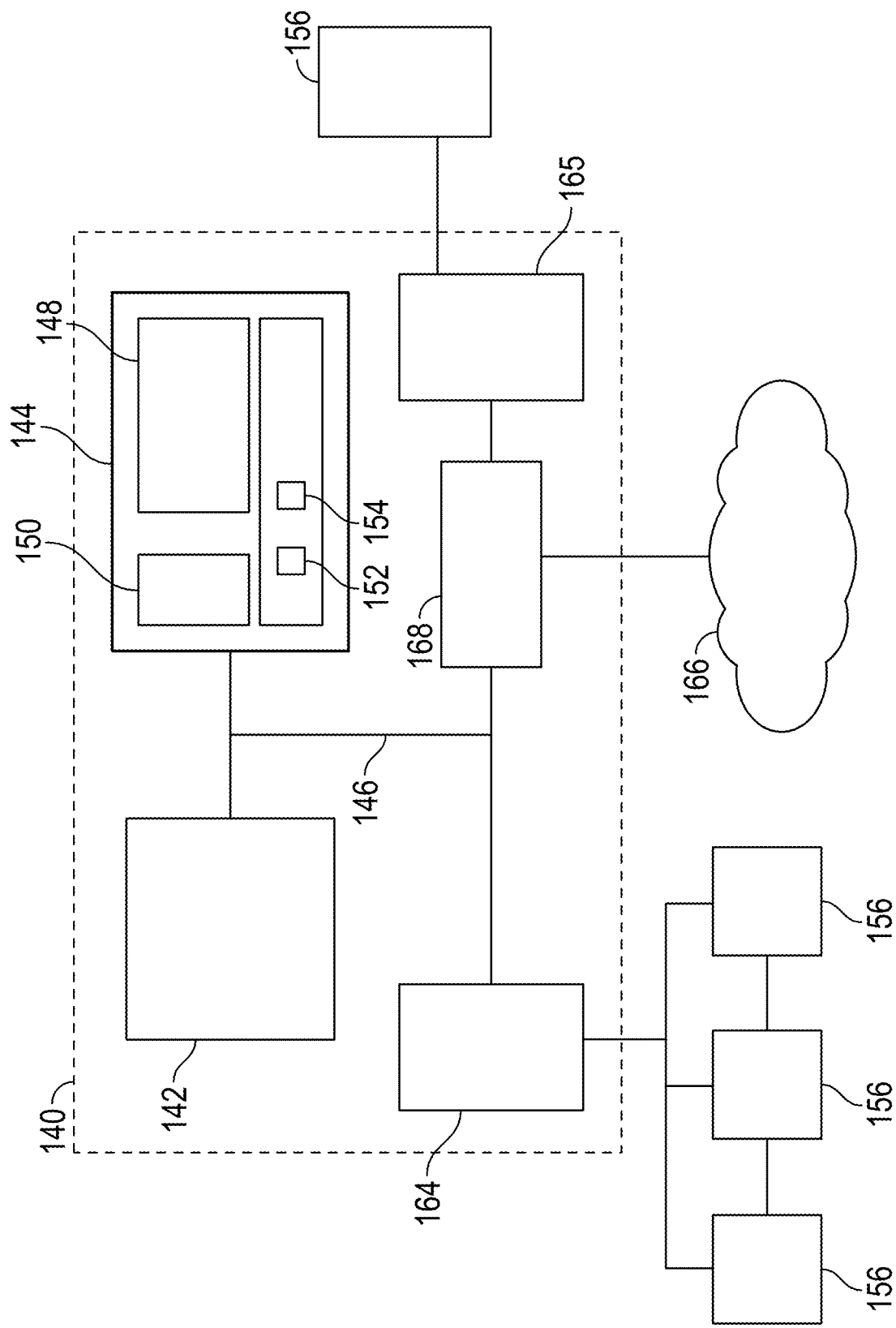
FIG. 11 depicts a computer system in accordance with an exemplary embodiment.

FIG. 11 illustrates aspects of an embodiment of a computer system 140 that can perform various aspects of embodiments described herein. The computer system 140 includes at least one processing device 142, which generally includes one or more processors for performing aspects of image acquisition and analysis methods described herein.

Components of the computer system 140 include the processing device 142 (such as one or more processors or processing units), a memory 144, and a bus 146 that couples various system components including the system memory 144 to the processing device 142. The system memory 144 may include a variety of computer system readable media. Such media can be any available media that is accessible by the processing device 142, and includes both volatile and non-volatile media, and removable and non-removable media.

For example, the system memory 144 includes a non-volatile memory 148 such as a hard drive, and may also include a volatile memory 150, such as random access memory (RAM) and/or cache memory. The computer system 140 can further include other removable/non-removable, volatile/non-volatile computer system storage media.

The system memory 144 can include at least one program product having a set (e.g., at least one) of program modules that are configured to carry out functions of the embodiments described herein. For example, the system memory 144 stores various program modules that generally carry out the functions and/or methodologies of embodiments described herein. A module or modules 152 may be included to perform functions related to acquiring images and/or controlling scanning speed and operational parameters. An image analysis module 154 may be included for analysis of images as described herein. The system 140 is not so limited, as other modules may be included. As used herein, the term "module" refers to processing circuitry that may include an application specific integrated circuit (ASIC), an electronic circuit, a processor (shared, dedicated, or group) and memory that executes one or more software or firmware programs, a combinational logic circuit, and/or other suitable components that provide the described functionality.

The processing device 142 can also communicate with one or more external devices 156 as a keyboard, a pointing device, and/or any devices (e.g., network card, modem, etc.) that enable the processing device 52 to communicate with one or more other computing devices. Communication with various devices can occur via Input/Output (I/O) interfaces 164 and 165.

The processing device 142 may also communicate with one or more networks 166 such as a local area network (LAN), a general wide area network (WAN), a bus network and/or a public network (e.g., the Internet) via a network adapter 168. It should be understood that although not shown, other hardware and/or software components may be used in conjunction with the computer system 40. Examples include, but are not limited to: microcode, device drivers, redundant processing units, external disk drive arrays, RAID systems, and data archival storage systems, etc.

While the above disclosure has been described with reference to exemplary embodiments, it will be understood by those skilled in the art that various changes may be made and equivalents may be substituted for elements thereof without departing from its scope. In addition, many modifications may be made to adapt a particular situation or material to the teachings of the disclosure without departing from the essential scope thereof. Therefore, it is intended that the present disclosure not be limited to the particular embodiments disclosed, but will include all embodiments falling within the scope thereof.

What is claimed is:

1. A system for inspecting a reflective surface, comprising:
a first imaging assembly including a first camera configured to take a first image of the reflective surface, the first image including depth information;
a second imaging assembly configured to take a second image of the reflective surface, the second image including contrast information, the second imaging assembly including a second camera and an illumination device configured project a light beam on the reflective surface, the illumination device disposed at a selected distance from the reflective surface and oriented according to a selected angle relative to the reflective surface, wherein the selected distance and the selected angle are determined by taking a plurality of reference images of a reference surface, each of the plurality of reference images taken with a respective combination of a distance value and an angle value, and selecting the angle value associated with a reference image having a highest homogeneity; and
a processor configured to acquire the first image and the second image, the processor configured to perform:
estimating a depth profile of the reflective surface based on the depth information;
correlating the depth profile with the second image; and
identifying a feature of the reflective surface based on the correlation.

2. The system of claim 1, wherein the reflective surface is a braze joint surface.

3. The system of claim 1, wherein correlating the depth profile with the second image includes constructing an image having an image attribute that is based on the depth profile.

4. The system of claim 1, wherein the first imaging assembly includes a laser oriented toward the reflective surface, the laser configured to project a laser line on the reflective surface, the first image including a series of images, each of the series of images depicting the laser line at a plurality of locations along the reflective surface.

5. The system of claim 4, wherein the depth profile is estimated based on based on a laser triangulation technique.

6. The system of claim 4, wherein the illumination device is configured project a diffuse light beam on the reflective surface.

7. The system of claim 6, wherein the first imaging assembly and the second imaging assembly are in a fixed position relative to one another, and the first imaging assembly and the second imaging assembly are configured to be scanned along the reflective surface and take the first image and the second image simultaneously.

8. The system of claim 1, wherein a homogeneity of each reference image of the plurality of reference images is estimated based on an intensity distribution calculated for each reference image.

9. The system of claim 1, wherein the selected distance is the distance value associated with the determined reference image having the highest homogeneity.

10. The system of claim 3, wherein identifying the feature includes selecting an image window corresponding to a section of the constructed image, the image window having a size selected based on an expected size of the feature.

11. A method of inspecting a reflective surface, comprising:
taking a first image of the reflective surface by a first camera of a first imaging assembly, the first image including depth information;
taking a second image of the reflective surface by a second imaging assembly, the second image including contrast information, the second imaging assembly including a second camera and an illumination device configured project a light beam on the reflective surface, the illumination device disposed at a selected distance from the reflective surface and oriented according to a selected angle relative to the reflective surface, wherein the selected distance and the selected angle are determined by taking a plurality of reference images of a reference surface, each of the plurality of reference images taken with a respective combination of a distance value and an angle value, and selecting the angle value associated with a reference image having a highest homogeneity;
estimating a depth profile of the reflective surface based on the depth information;
correlating the depth profile with the second image; and
identifying a feature of the reflective surface based on the correlation.

12. The method of claim 11, wherein correlating the depth profile with the second image includes constructing an image having an image attribute that is based on the depth profile.

13. The method of claim 11, wherein the first imaging assembly includes a laser oriented toward the reflective surface, the laser configured to project a laser line on the reflective surface, wherein taking the first image includes taking a series of images, each of the series of images depicting the laser line at a plurality of locations along the reflective surface.

14. The method of claim 13, wherein the illumination device is configured project a diffuse light beam on the reflective surface.

15. The method of claim 11, wherein the selected distance is the distance value associated with the determined reference image having the highest homogeneity.

16. The method of claim 12, wherein identifying the feature includes selecting an image window corresponding to a section of the constructed image, the image window having a size selected based on an expected size of the feature.

17. The method of claim 16, wherein the size of the window is selected based on a machine learning model.

18. A computer program product comprising a computer readable storage medium, the computer readable storage medium having instructions executable by a computer processor to cause the computer processor to perform a method comprising:
taking a first image of a reflective surface by a first camera of a first imaging assembly, the first image including depth information;
taking a second image of the reflective surface by a second imaging assembly, the second image including contrast information, the second imaging assembly including a second camera and an illumination device configured project a light beam on the reflective surface, the illumination device disposed at a selected distance from the reflective surface and oriented according to a selected angle relative to the reflective surface, wherein the selected distance and the selected angle are determined by taking a plurality of reference images of a reference surface, each of the plurality of reference images taken with a respective combination of a distance value and an angle value, and selecting the angle value associated with a reference image having a highest homogeneity;

estimating a depth profile of the reflective surface based on the depth information;

correlating the depth profile with the second image; and identifying a feature of the reflective surface based on the correlation.

19. The computer program product of claim 18, wherein the first imaging assembly includes a first camera and a laser oriented toward the reflective surface, the laser configured to project a laser line on the reflective surface, wherein taking the first image includes taking a series of images, each of the series of images depicting the laser line at a plurality of locations along the reflective surface.

20. The computer program product of claim 19, wherein the illumination device is configured project a diffuse light beam on the reflective surface.

* * * * *